United States Patent [19]

Gsell

[11] Patent Number: 4,948,798
[45] Date of Patent: Aug. 14, 1990

[54] SUBSTITUTED CYANOIMINOIMIDAZOLIDINES AND -TETRAHYDROPYRIMIDINES USEFUL AS PESTICIDES

[75] Inventor: Laurenz Gsell, Basel, Switzerland

[73] Assignee: Ciba-Geigy Corporation, Ardsley, N.Y.

[21] Appl. No.: 396,588

[22] Filed: Aug. 21, 1989

Related U.S. Application Data

[63] Continuation-in-part of Ser. No. 226,357, Jul. 29, 1988, abandoned.

[30] Foreign Application Priority Data

Aug. 4, 1987 [CH] Switzerland ............... 2985/87
Jun. 6, 1988 [CH] Switzerland ............... 2141/88

[51] Int. Cl.$^5$ ............... C07D 401/06; A01N 43/50; A01N 43/54
[52] U.S. Cl. ............... 514/275; 514/341; 544/331; 546/278
[58] Field of Search ............... 544/331; 546/278; 514/275, 341

[56] References Cited

U.S. PATENT DOCUMENTS

| | | | |
|---|---|---|---|
| 2,697,727 | 12/1954 | Kaiser et al. | 558/4 |
| 3,074,955 | 1/1963 | Shapiro et al. | 546/330 |
| 4,098,791 | 7/1978 | Hylteen et al. | 546/246 |
| 4,647,570 | 3/1987 | Shiokawa et al. | 514/341 |
| 4,678,795 | 7/1987 | Shiokawa et al. | 514/341 |
| 4,680,294 | 7/1987 | Shiokawa et al. | 514/256 |
| 4,707,478 | 11/1987 | Studt et al. | 514/580 |

FOREIGN PATENT DOCUMENTS

| | | |
|---|---|---|
| 126558 | 11/1984 | European Pat. Off. |
| 235725 | 9/1987 | European Pat. Off. |
| 1443913 | 11/1972 | Fed. Rep. of Germany |
| 3148103 | 6/1983 | Fed. Rep. of Germany |

OTHER PUBLICATIONS

Journal of Medicinal Chemistry, vol. 21, No. 8, 1978, pp. 773-781.
Journal of Heterocyclic Chem, vol. 23 (1986), pp. 401-408.
Chemical Abstract, vol. 85 (1976), 159372z.
Journal of Praktische Chemie, vol. 318, 1976, pp. 479-482.
Arch. Pharm. 310, pp. 820-827 (1977).
Arch. Pharm. 320, pp. 617-620 (1987).
Journal of Praktische Chemie, vol. 323 (1981), pp. 694-699.
Arzneim-Forsch/Drug Res. 29 (I) Nr 4 (1979).
Yuki Gosei Kagaku Kyokai Shi, vol. 29, No. 1, 1971.
Chem. Ber 101, 3185-3200 (1968).
Chem. Ber 100, 2604-2615 (1967).
Chemical Abstract, vol. 90, 87289f (1979).

Primary Examiner—Richard A. Schwartz
Assistant Examiner—Richard A. Sharpe
Attorney, Agent, or Firm—Kevin T. Mansfield

[57] ABSTRACT

Novel substituted pyridylmethyl-cyanoiminoimidazolidines and pyridylmethyl-cyanoiminotetrahydropyrimidines of the formula

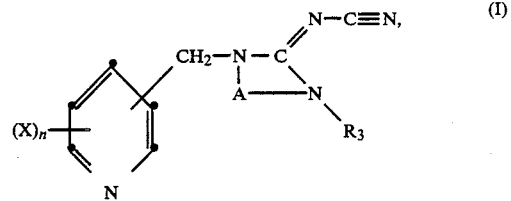

in which $R_3$ is hydrogen or $C_1-C_4$alkyl; A is a $-(CH_2)_2-$ or $-(CH_2)_3-$ radical; X is halogen; and n is an integer 0, 1, 2 or 3; and the salts of compounds of formula I. Also described is a process for the preparation of these compounds, the corresponding starting materials and intermediates, and the use of the novel compounds in pest control, especially for controlling insects and representatives of the order Ararina, particularly insect pests in rice crops.

13 Claims, No Drawings

SUBSTITUTED CYANOIMINOIMIDAZOLIDINES AND -TETRAHYDROPYRIMIDINES USEFUL AS PESTICIDES

The present invention relates to novel substituted pyridylmethyl-cyanoiminoimidazolidines and pyridylmethyl-cyanoiminotetrahydropyrimidines and to their use in controlling pests.

The invention relates to novel compounds of formula I

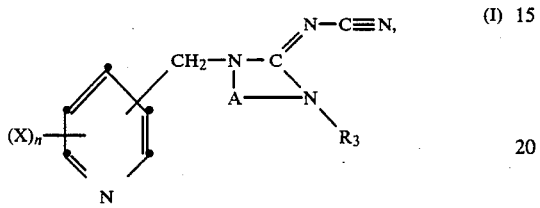 (I)

in which $R_3$ is hydrogen or $C_1$-$C_4$alkyl; A is a —(CH$_2$)$_2$— or —(CH$_2$)$_3$— radical; X is halogen; and n is an integer 0, 1, 2 or 3; and to the salts of compounds of formula I.

Compounds of formula I according to the invention in which $R_3$ is hydrogen or methyl; X is chlorine and n is an integer 0, 1 or 2, are preferred.

Attention is drawn especially to compounds of formula I in which n is 0.

Also preferred are those compounds of formula I according to the invention in which $R_3$ is hydrogen, methyl or ethyl; and n is the integer 0.

Owing to their biological activity, those compounds of formula I according to the invention in which the pyridyl radical is pyrid-3-yl or pyrid-4-yl are of particular interest.

There is to be understood by "alkyl", on its own or as a component of another substituent, a straight-chained or branched alkyl group and, depending on the number of carbon atoms indicated within the scope of the present invention, for example one of the following groups: methyl, ethyl, propyl, butyl, and the isomers thereof, such as isopropyl, cyclopropyl, isobutyl, tert.-butyl and sec.-butyl.

The term "halogen" within the scope of the present invention is to be understood as meaning fluorine, chlorine and bromine, preferably fluorine and chlorine.

The present invention also relates to salts, especially non-toxic salts physiologically tolerated by plants, of compounds of formula I. The following, for example, are suitable salts of this kind with organic and inorganic acids: chlorides, bromides, iodides, sulfates, hydrogen sulfates, chlorates, perchlorates, thiocyanates, nitrates, phosphates, hydrogen phosphates, tetrafluoroborates, formates, acetates, trichloroacetates, trifluoroacetates, phenylsulfonates, oxalates, malonates, succinates, malates, tartrates and citrates.

The compounds of formula I and salts thereof can be prepared by reacting a compound of formula II

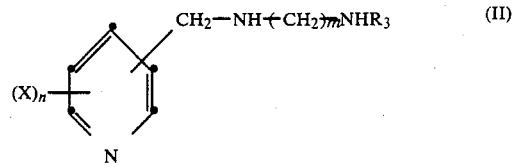 (II)

with a compound of formula III

 (III)

wherein in formulae II and III $R_3$ is hydrogen or $C_1$-$C_4$alkyl; X is halogen; n is an integer 0, 1, 2 or 3; m is an integer 2 or 3; and $Y_1$ and $Y_2$ are removable leaving groups; and, if desired, a compound of formula I obtained is converted in a manner known per se into one of its salts.

Within the scope of the process described above, suitable removable leaving groups in starting compounds of formula III are, for example, as follows:

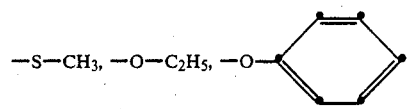

The above process resulting in the compounds of formula I according to the invention are preferably carried out in a solvent. Suitable solvents are, for example, aromatic hydrocarbons, such as benzene, toluene and xylene; ketones, such as acetone, cyclohexanone and methyl ethyl ketone; ethers, such as tetrahydrofuran, dioxan and diethyl ether; halogenated hydrocarbons, such as chloroform, carbon tetrachloride and chlorobenzene; alcohols, such as ethanol and propanol; esters of aliphatic acids, such as ethyl acetate; aliphatic amides, such as dimethylformamide and dimethylacetamide; dimethyl sulfoxide, acetonitrile and other solvents that do not impair the reaction. These solvents can also be used in the form of mixtures. The reaction temperature may be in a wide range of from $-10°$ to $+150°$ C. A temperature range of approximately from $20°$ to $80°$ C. is preferred.

The above described ring closure reaction for preparing compounds of formula I is known per se and are set forth in principle in U.S. Pat. No. 4,678,795.

The starting compounds of formulae II and III are known and can be obtained analogously to known methods. Picolylamine compounds of formula II are known or can be obtained analogously to known processes [cf. U.S. Pat. No. 4,678,795; Tetrahedron Letters 26, 5863 (1985)].

Certain pyridylmethyl-nitroiminoimidazolines and -tetrahydropyrimidines, their preparation and their use as insecticides have already been described in U.S. Pat. No. 4,678,795.

It has now surprisingly been found that the novel compounds of formula I according to the invention have excellent insecticidal properties while being well tolerated by plants and having low toxicity to warm-blooded animals. They are suitable especially for controlling pests that attack plants and animals.

The compounds of formula I are especially suitable for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and representatives of the order Acarina.

The good pesticidal activity of the compounds of the invention corresponds to a mortality rate of at least 50–60% of the pests mentioned.

Using the compounds of formula I of the invention it is possible especially for plant-damaging insects, especially plant-damaging insects in crops of ornamental and useful plants, especially cotton crops, vegetable crops, rice crops and fruit crops, to be controlled. In this connection, attention is drawn to the fact that the said compounds are distinguished by a strongly pronounced systemic action, but especially by contact action, against sucking insects, especially against insects of the Aphididae family (such as, for example, Aphis fabae, Aphis craccivora and Myzus persicae), that can be controlled by conventional compositions only with difficulty.

The compounds of formula I are furthermore distinguished by a good activity against larval insect stages and against nymphs, especially of feeding insect pests. In particular, the compounds of formula I can be used with excellent success against plant-damaging cicadas, especially in rice crops. In this connection attention is drawn to the low toxicity to fish of the compounds of the invention.

The compounds are also suitable for controlling ectoparasites, for example Lucilia sericata, and ticks on domestic animals and productive livestock, for example by treating the animals, livestock buildings and pastures.

The activity of the compounds of the invention and of compositions containing them can be broadened substantially and adapted to the given circumstances by adding other insecticides and/or acaricides. Possible additives are, for example, representatives of the following classes of active substance: organic phosphorus compounds, nitrophenols and derivatives, formamidines, ureas, carbamates, pyrethroids, chlorinated hydrocarbons and Bacillus thuringiensis preparations.

The compounds of formula I are used in unmodified form or, preferably, together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the active ingredient or combinations of these active ingredients with other insecticides or acaricides and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane, paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Depending on the nature of the active ingredient of formula I to be formulated, or of the combination of these active ingredients with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil. Other suitable surfactants that may be mentioned are fatty acid methyltaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately from 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are especially polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are especially quaternary ammonium salts that contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customary in the art of formulation are described inter alia in the following publications:
"Mc Cutcheon's Detergents and Emulsifiers Annual" MC Publishing Corp., Ridgewood, N.J., 1979;
Dr. Helmut Stache "Tensid Taschenbuch", Carl Hanser Verlag, Munich/Vienna 1981.

The pesticidal formulations usually contain—based on weight—0.1 to 99%, especially 0.1 to 95%, of an active ingredient of formula I or combinations thereof with other insecticides or acaricides, 1 to 99.9% of a solid or liquid adjuvant, and 0 to 25%, especially 0.1 to 20%, of a surfactant. Whereas commercial products will preferably be formulated as concentrates, the end user will normally employ dilute formulations containing substantially lower concentrations of active ingredient, for example from 0.1 to 1000 ppm.

The compositions may also contain further adjuvants such as stabilisers, antifoams, viscosity regulators, binders, tackifiers as well as fertilisers or other active ingredients for obtaining special effects.

EXAMPLE 1

Preparation of 1-(pyrid-3-ylmethyl)-2-cyanoiminoimidazolidine 7.56 g of N-pyrid-3-ylmethylethylenediamine, 7.31 g of dimethyl-N-cyanothioiminocarbonate and 20 mg of dimethylaminopyridine in 50 ml of acetonitrile are heated at reflux for 3 hours. The product crystallises out when the mixture has cooled. The resulting crystals are filtered off and washed with ether, yielding the title compound of formula

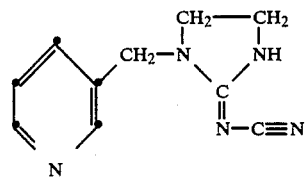

having a melting point of 126.5°–128.5° C. (compound No. 1).

The following compounds of formula I are prepared in the manner indicated above:

| Compound No. | pyridyl position | A | $R_3$ | n | X | physical data |
|---|---|---|---|---|---|---|
| 2 | 4— | $(CH_2)_2$ | H | 0 | — | mp = 187–189° C. |
| 3 | 2— | $(CH_2)_2$ | H | 0 | — | mp = 167–168.5° C. |
| 4 | 5— | $(CH_2)_2$ | H | 2 | 2-Cl 3-Cl | mp = 193–197° C. |
| 5 | 5— | $(CH_2)_2$ | H | 1 | 2-Cl | mp = 161–163.5° C. |

It is also possible to prepare the following compounds of formula I analogously to the procedures described above:

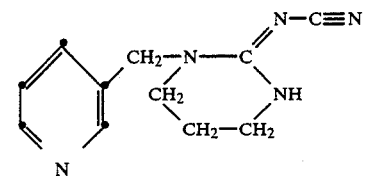

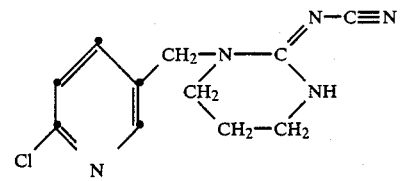

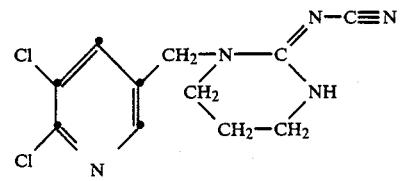

EXAMPLE 2

Formulations for active ingredients of formula I according to Example 1, or for combinations of these active ingredients with other insecticides or acaricides (%=percent by weight)

| 1. Wettable powders | (a) | (b) | (c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or the active ingredient combination is mixed with the adjuvants and the mixture is thoroughly ground in a suitable mill, affording wettable powders which can be diluted with water to give suspensions of the desired concentration.

| 2. Emulsifiable concentrate | |
|---|---|
| active ingredient or active ingredient combination | 10% |

-continued

| 2. Emulsifiable concentrate | |
|---|---|
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| active ingredient or active ingredient combination | 5% | 8% |
| talcum | 95% | — |
| kaolin | — | 92% |

Ready-for-use dusts are obtained by mixing the active ingredient with the carrier and grinding the mixture in a suitable mill.

| 4. Extruder granulate | |
|---|---|
| active ingredient or active ingredient combination | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded, granulated and then dried in a stream of air.

| 5. Coated granulate | |
|---|---|
| active ingredient or active ingredient combination | 3% |
| polyethylene glycol (MW 200) | 3% |
| kaolin | 94% |

The finely ground active ingredient or the active ingredient combination is uniformly applied, in a mixer, to the kaolin moistened with polyethylene glycol. Non-dusty coated granulates are obtained in this manner.

| 6. Suspension concentrate | |
|---|---|
| active ingredient or active ingredient combination | 40% |
| ethylene glycol | 10% |
| nonylphenol polyethylene glycol ether (15 moles of ethylene oxide | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or the active ingredient combination is intimately mixed with the adjuvants, giving a suspension concentrate from which suspensions of any desired concentration can be obtained by dilution with water.

EXAMPLE 3

Action against *Lucilia sericata*

1 ml of an aqueous formulation containing 0.1% active ingredient is added at 50° C. to 9 ml of a culture medium. Approximately 30 newly hatched Lucilia sericata larvae are then added to the culture medium. The insecticidal action is determined after 48 and 96 hours by ascertaining the mortality rate.

Compounds of formula I according to Example 1 exhibit a good activity (mortality rate) against Lucilia sericata in this test.

EXAMPLE 4

Action against *Aedes aegypti*

A 0.1% solution of the active ingredient in acetone is pipetted onto the surface of 150 ml of water in a container in an amount sufficient to produce a concentration of 400 ppm. When the acetone has evaporated the container is charged with from 30 to 40 2 day-old Aedes larvae. The percentage mortality (number of larvae unable to swim) is assessed after 2 and 7 days.

Compounds of formula I according to Example 1 exhibit a good activity (mortality rate) in this test.

EXAMPLE 5

Insecticidal contact action: *Aphis craccivora*

Before the beginning of the test, plants (*Vicia faba*) grown in pots are each populated with about 200 specimens of the species *Aphis craccivora*. 24 hours later, the plants treated in this manner are sprayed to drip point with an aqueous formulation containing 400 ppm of the test compound. Two plants are used per test compound, and an evaluation of the mortality rate achieved is carried out after a further 24 hours.

Compounds of formula I according to Example 1 exhibit a good activity (mortality rate) in this test.

EXAMPLE 6

Systemic insecticidal action: *Aphis craccivora*

Rooted bean plants are planted in pots containing 600 ccm of soil. 50 ml of a formulation of the test compound (obtained from a 25% wettable powder), in a concentration of 400 ppm, is then poured directly onto the soil in each pot.

After 24 hours aphids of the species *Aphis craccivora* are placed on the parts of the plant above soil level and a plastics cylinder is slipped over the plants in order to protect the aphids from any possible contact action or gas action of the test substance.

An evaluation of the mortality rate achieved is made 48 and 72 hours after the beginning of the test. Two plants, each in a separate pot, are used per test substance. The test is carried out at 25° C. and 70% relative humidity.

The compounds of formula I according to Example 1 exhibit a good activity in this test.

EXAMPLE 7

Insecticidal contact action: *Myzus persicae*

Pea seedlings approximately 4 cm high that have been grown in water are each populated before the beginning of the test with about 200 specimens of the species *Myzus persicae*. The plants treated in this manner are 24 hours later sprayed to drip point with an aqueous suspension containing 400 ppm of the test compound.

Two plants are used per compound and concentration. An evaluation of the mortality rate achieved is carried out 48 hours after application. The test is carried out at from 20 to 22° C. and 60% relative humidity.

The compounds of formula I according to Example 1 exhibit a good activity in this test.

EXAMPLE 8

Systemic insecticidal action: *Myzus persicae*

Rooted cabbage plants at the 4- to 5-leaf stage are transplanted into pots containing 60 ccm of soil. 50 ml of an aqueous formulation of test compound of formula I (obtained from a 25% wettable powder), in each case in a concentration of 400 ppm, are then poured directly onto the soil.

After 24 hours aphids of the species *Myzus persicae* are placed on the parts of the treated plants that are above soil level and plastics cylinders are slipped over the plants in order to protect the aphids from any possible contact action or gas action of the test substance. An evaluation of the percentage mortality achieved is made 48 hours after the beginning of the test. Two plants, each in a separate pot, are used per test substance. The test is carried out at approximately 25° C. and 60% relative humidity.

The compounds of formula I according to Example 1 exhibit a good activity in this test.

EXAMPLE 9

Insecticidal leaf penetration action: *Aphis craccivora*

A suitably small sprig of Vicia faba heavily infested with aphids of the species *Aphis craccivora* is placed into each of a number of plastics beakers approximately 8 cm in height (diameter approximately 6 cm). Each beaker is covered with a plastics lid that has a hole of 2 cm diameter punched in the middle. A leaf of a *Vicia faba* plant is placed on the hole in the lid without this leaf being separated from the potted plant. The leaf is then fixed by a second perforated lid on the beaker over the hole in the first lid. From the underside, that is to say through the hole in the first lid, the aphids in the beaker then infest the overlying leaf of the feed plant. An aqueous preparation of the test compound is uniformly applied in a concentration of 400 ppm to the upper side of the leaf using a brush. An examination is made to determine whether the test substance applied to the upper side of the leaf of the feed plant has diffused through the leaf to the underside thereof in an amount that is sufficient to kill the aphids sucking there.

The test is carried out at approximately 20° C. and 60% relative humidity. The evaluation for percentage mortality is carried out 48 hours after application of the active ingredient.

Compounds of formula I according to Example 1 exhibit a good activity in this test.

EXAMPLE 10

Insecticidal action (systemic-water): *Aphis craccivora*

Pea seedlings that have been infested with aphids 24 hours before the beginning of the test are placed in 20 ml of an aqueous mixture containing 400 ppm of the test compound. The aqueous mixture is prepared from an emulsifiable concentrate or a wettable powder formulation of the active ingredient in question and is contained in a vessel sealed with a plastics lid having holes. The roots of the infested pea plants are each pushed into the mixture through a hole in the plastics lid. The hole is then sealed with cotton wool in order to fix the plant in position and prevent any possible influence from the gaseous phase of the mixture.

The test is carried out at 20° C. and 60% relative humidity. After 2 days the number of test insects no longer able to suck is evaluated by comparison with untreated controls. By this means it is possible to determine whether the active ingredient taken up through the roots kills the aphids on the upper parts of the plants.

Compounds of formula I according to Example 1 exhibit a good systemic action against insects of the species Aphis craccivora in this test.

EXAMPLE 11

Stomach toxicant action and contact action on *Laodelphax striatellus* and *Nilaparvata lugens* (nymphs)

The test is carried out on growing plants. For this purpose in each case 4 rice plants (thickness of the stem 8 mm) approximately 20 cm in height are planted into pots (8 cm in diameter).

The plants are sprayed on a rotarytable with 100 ml of a solution in acetone containing 400 ppm of the active ingredient in question. When the spray coating has dried, each plant is populated with 20 nymphs of the test insects in the third stage. To prevent the cicadas from escaping, a glass cylinder open at both ends is slipped over each of the populated plants and this cylinder is closed with a gauze lid. The nymphs are kept on the treated plant over a period of 10 days until they have reached the next stage of development. An evaluation of the percentage mortality is made 1, 4 and 8 days after the treatment.

Compounds of formula I according to Example 1 exhibit a good activity against *Nilaparvata lugens* in this test.

EXAMPLE 12

Systemic action on *Nilaparvata lugens*

Approximately 10 day-old rice plants (approximately 10 cm high) are each placed in a plastics beaker containing 20 ml of an aqueous emulsion formulation of the test compound in a concentration of 400 ppm that is closed with a plastics lid having holes. The roots of the rice plants are in each case pushed through a hole in the plastics lid into the aqueous test formulation. The hole is then sealed with cotton wool in order to fix the plant in position and prevent any possible influence from the gaseous phase of the test formulation. The rice plant is then populated with 20 nymphs of Nilaparvata lugens in the N 2 to N 3 stage and covered with a plastics cylinder. The test is carried out at 20° C. and 60% relative humidity with an light exposure period of 16 hours. After 5 days the number of dead test insects is evaluated by comparison with untreated controls. By this means it is possible to determine whether the active ingredient taken up through the roots kills the test insects on the upper parts of the plants.

Compounds of formula I according to Example 1 exhibit a good activity (mortality rate) against *Nilaparvata lugens* in this test.

EXAMPLE 13

Insecticidal stomach toxicant action and contact action

Potted cotton plants approximately 25 cm high are sprayed with aqueous emulsions containing the active ingredient in a concentration of 800 ppm.

When the spray coating has dried the cotton plants are populated with *Spodoptera littoralis* and *Heliothis virescens* larvae in the first larval stage. The test is carried out at 24° C. and approximately 60% relative humidity. After 120 hours the percentage mortality of the test insects is ascertained by comparison with untreated controls.

Compounds of formula I according to Example 1 exhibit a good activity (mortality rate) in this test.

EXAMPLE 14

Action against *Nephotettix cincticeps* (nymphs)

The test is carried out on growing plants. For this purpose approximately 20 day-old rice plants about 15 cm in height are planted into pots (diameter 5.5 cm).

The plants are each sprayed on a turntable with 100 ml of a solution in acetone containing 400 ppm of the test compound. After the spray coating has dried, each plant is populated with about 20 nymphs of the test insects in the second or third stage. In order to prevent the cicadas from escaping, a plexiglass cylinder is slipped over each of the populated plants and closed with a gauze lid. The nymphs are kept for 5 days on the treated plants, which have to be watered at least once. The test is carried out at a temperature of approximately 23° C. at 55% relative humidity and with an light exposure period of 16 hours.

Compounds of formula I according to Example 1 exhibit a good activity in this test.

What is claimed is:

1. A compound of formula I

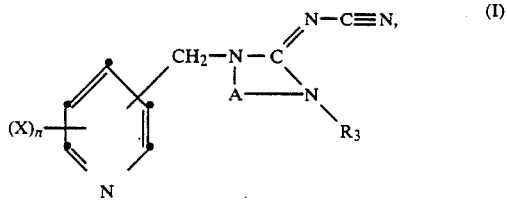

in which $R_3$ is hydrogen or $C_1$-$C_4$alkyl; A is a —$(CH_2)_2$— or —$(CH_2)_3$— radical; X is halogen; and n is an integer 0, 1, 2 or 3; the salt of the compound of formula I.

2. A compound of formula I according to claim 1, wherein $R_3$ is hydrogen or methyl; X is chlorine and n is an integer 0, 1 or 2.

3. A compound according to claim 1, wherein n is the integer 0.

4. A compound of formula I according to claim 1, wherein $R_3$ is hydrogen, methyl or ethyl; and n is the integer 0, 1, 2 or 3.

5. A compound of formula I according to claim 1, wherein $R_3$ is hydrogen.

6. A compound of formula I according to claim 1, wherein the pyridyl radical is a pyrid-3-yl or pyrid-4-yl radical.

7. A compound according to claim 6 of formula

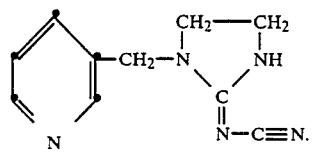

8. A compound according to claim 6 of formula

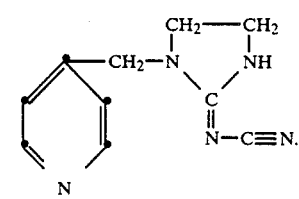

9. A compound according to claim 2 of formula

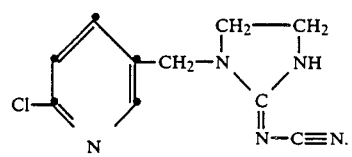

10. A compound according to claim 2 of formula

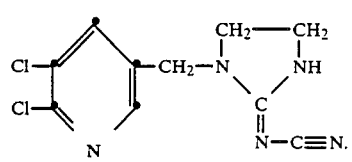

11. A composition for controlling insect pests and pests of the order Acarina containing as active component at least one compound of formula I according to claim 1.

12. A method of controlling insects and representatives of the order of Acarina which comprises bringing into contact or treating the pests, or various stages of development thereof or the locus thereof, with a pesticidally effective amount of a compound of formula I according to claim 1.

13. A method according to claim 12 for controlling feeding insect pests in rice crops.

* * * * *